United States Patent

Serbousek et al.

[11] Patent Number: 5,916,269
[45] Date of Patent: *Jun. 29, 1999

[54] WEAR REDUCED ACETABULAR COMPONENT

[75] Inventors: Jon Serbousek, Winona Lake; Frank S. Bono, Warsaw, both of Ind.

[73] Assignee: DePuy Orthopaedics, Inc., Warsaw, Ind.

[*] Notice: This patent issued on a continued prosecution application filed under 37 CFR 1.53(d), and is subject to the twenty year patent term provisions of 35 U.S.C. 154(a)(2).

[21] Appl. No.: 08/656,780

[22] Filed: Jun. 3, 1996

[51] Int. Cl.⁶ .............................. A61F 2/28; A61F 2/34; A61F 2/38; A61F 2/30
[52] U.S. Cl. .............................. 623/22; 623/16; 623/18; 623/20
[58] Field of Search .................. 623/22, 23, 16, 623/18, 20

[56] References Cited

U.S. PATENT DOCUMENTS

| | | |
|---|---|---|
| 4,031,570 | 6/1977 | Frey .......................................... 623/22 |
| 4,068,324 | 1/1978 | Townley et al. . |
| 4,156,296 | 5/1979 | Johnson et al. . |
| 4,676,798 | 6/1987 | Noiles . |
| 4,731,088 | 3/1988 | Collier . |
| 4,755,185 | 7/1988 | Tarr . |
| 4,822,366 | 4/1989 | Bolesky . |
| 4,822,369 | 4/1989 | Oueveau ..................................... 623/22 |
| 4,904,265 | 2/1990 | MacCollum et al. . |
| 4,964,867 | 10/1990 | Boger . |
| 5,002,577 | 3/1991 | Bolesky et al. . |
| 5,009,665 | 4/1991 | Serbousek et al. . |
| 5,032,132 | 7/1991 | Matsen, III et al. . |
| 5,147,405 | 9/1992 | Van Zile et al. . |
| 5,194,066 | 3/1993 | Van Zile . |
| 5,549,700 | 8/1996 | Graham et al. ........................... 623/22 |

FOREIGN PATENT DOCUMENTS

| | | |
|---|---|---|
| 2626766 | 8/1989 | France ........................................ 2/32 |
| 2229812 | 1/1974 | Germany . |

OTHER PUBLICATIONS

Harlan C. Amstutz, M.D. and Peter Grigoris, M.D., Ph.D., *Metal on Metal Bearings in Hip Arthroplasty*, Clinical Orthopaedics and Related Research, No. 329S, Aug. 1996.

*Primary Examiner*—David H. Willse
*Assistant Examiner*—John M. Black
*Attorney, Agent, or Firm*—Barnes & Thornburg

[57] ABSTRACT

A bearing component includes an interrupted articular face suitable for mating with a corresponding joint face. The interrupted articular face of the bearing component is defined by a plurality of bearing platforms integral with the face where either recesses extend between the bearing platforms or said platforms protrude from the articular face in order to minimize surface area of articulation for the corresponding joint face.

26 Claims, 4 Drawing Sheets

WEAR REDUCED ACETABULAR COMPONENT

BACKGROUND AND SUMMARY OF THE INVENTION

The present invention relates to an improved component for a prosthesis assembly used in replacing a natural joint. More particularly, the present invention relates to a prosthetic component designed to include an interrupted articular face for minimizing surface area of articulation between itself and either a natural or prosthetic member.

It is known to provide a prosthetic joint assemblies for acetabulums, knees, ankles, shoulders, elbows, and wrists. Components of prosthetic joints such as that shown in U.S. Pat. No. 4,068,342 to Townley et al., provide a face having a continuous surface area of articulation for its corresponding member. While conventional prosthetic components beneficially provide a low-friction articular face for the surface of accompanying member, interaction between the articulating component and the member can produce joint debris. Such debris is expelled into the patient and may cause adverse reactions in the surrounding bodily tissue.

Attempts have been made to prevent joint debris produced by prosthesis joint assemblies from entering surrounding bodily tissue. See for example, U.S. Pat. No. 4,731,088 to Collier, where a flexible enclosure is applied to a prosthetic joint to isolate the joint debris from the surrounding tissue. What is needed is an improved bearing component for a prosthesis assembly which includes a face that is formed to minimize surface area of articulation for the engaging accompanying member and thus minimize the production of joint debris.

One object of the present invention is to provide an improved prosthetic component for use in a prosthesis which includes a surface that minimizes the production of joint debris produced from articulating movement of a corresponding member on said surface.

Another object of the present invention is to provide a bearing component for use in a prosthesis which includes an interior that forms an internal cavity suitable for receiving a ball therein, the cavity having an interrupted articular face for engaging the ball.

Still another object of the present invention is to provide a bearing component for use in a prosthesis which includes an interior that maximizes available ball distribution within said bearing component and minimizes the production of joint debris upon articulating movement of the ball.

Yet another object of the present invention is to provide an improved prosthetic component for use in a prothesis assembly which includes an interior that forms an internal cavity suitable for receiving a ball therein. The cavity being formed to enhance joint stability and reduce wear between the interior and the ball.

Another object of the present invention is to provide an improved prosthetic component for use in a prosthesis assembly which includes an interrupted articular face for engaging a corresponding articulating member.

According to one embodiment of the present invention a bearing component for a prosthesis of the ball-joint type, is provided. The bearing component provides a spherically concave bearing surface for receiving a ball, the surface being defined by a plurality of bearing platforms integral with said component. Thus, the bearing surface minimizes available surface area of articulation for the ball and the production of joint debris.

According to another aspect of the present invention a bearing component is provided for use with a ball. The bearing component has a generally hemispherical interior providing an internal cavity with an interrupted articular face. The interrupted articular face engages the ball and is interrupted by at least one recess extending into its bearing surface. In this specification and in the claims, the words "generally hemispherical" are intended to cover the spherical ranges conventionally used in acetabular and glenoid cup bearings including less than hemispherical and, in some cases, slightly more than hemispherical.

According to yet another aspect of the present invention a bearing component is provided for use with a ball. The bearing component comprises an interior having an internal cavity for receiving the ball therein. The cavity is defined by a one-piece articular face having a generally hemispherical bearing surface defined by at least one bearing platform extending into the internal cavity for engagement with the ball.

According to another embodiment of the present invention a ball component is provided for use with either a natural or prosthetic socket. The ball component comprises an interrupted articular socket-engaging face which effectively reduces surface area of articulation between the ball and the socket. The interrupted articular socket-engaging face rests against the socket and is interrupted by at least one recess extending into its surface. In this specification and in the claims, the words "ball component" are intended to cover prosthetic components for either the femoral or humeral head. Such ball components may be attached to an appropriate femoral or humoral stem.

According to another embodiment of the present invention a prosthetic patellar implant is provided for use with a natural or prosthetic knee. The patellar implant includes a patellum facing surface and a contoured interrupted surface opposite the patellum facing surface. The contoured interrupted surface engages either a natural or prosthetic distal end of a femur and is interrupted by a plurality of bearing platforms integral with said surface.

According to yet another embodiment of the present invention a prosthetic component is formed for replacing the extreme distal portion of the femur or the humorous and for attachment to either a prosthetic or natural femoral/humoral stem. The prosthetic component includes two interrupted condyles or articular surfaces that are configured to replace the smooth, uninterrupted condyles of the extreme distal portion. The condyles provide a convex interrupted bearing surface for engagement with medial and lateral condyles of a tibia or the condyle(s) of the radius and/or ulna. The interrupted articular surface of the prosthetic component is defined by a plurality of bearing platforms integral with the component.

According to yet another embodiment of the present invention, a prosthetic component is formed for replacing an extreme proximal portion of the tibia, radius, or ulna and in particular the medial and lateral condyles of the tibia or the condyle(s) of the radius and/or ulna. The prosthetic component is formed to include at least one slightly concave interrupted bearing surface. The interrupted bearing surfaces are formed to receive either a natural or prosthetic extreme distal portion of the femur or humorous, the surfaces being defined by a plurality of bearing platforms integral with the component. Thus, the bearing surface minimizes available surface area of articulation for the component and the production of joint debris.

The bearing components of the present invention are formed to reduce surface area of articulation between corresponding articulating bearing components. Because the articular face is interrupted by recesses and/or protrusions, the interrupted articulation surface will be maintained despite minimal wear that may occur at the point of contact between the bearing components. This reduction in surface area is intended to lead to a decrease in the production of joint debris which contributes to both wear debris incited osteolysis and eventually to failure of the prostheses assembly.

Other objects and features of the present invention will become apparent as this description progresses.

BRIEF DESCRIPTION OF THE DRAWINGS

The detailed description particularly refers to the accompanying figures in which.

DETAILED DESCRIPTION OF THE DRAWINGS

The present invention is based upon the discovery that a bearing component having an articular face, interrupted by either recesses or protrusions, minimizes production of joint debris created by the interaction between the face and an accompanying joint face articulation member. This decrease is believed to be the result of the reduction in available surface area of articulation between the members, in comparison with traditional bearing components having smooth uninterrupted articulation faces. Beneficially, one bearing component in accordance with the present invention allow physicians to utilize a large ball diameter for enhancement of joint stability while increasing lubrication and minimizing the production of undesirable joint debris when replacing a patient's ball-type joint with a prosthetic assembly. Further, beneficially other bearing components in accordance with the present invention allows a physician to increase lubrication and minimize the production of undesirable joint debris when replacing a patient's hip, shoulder, knee, elbow, ankle, wrist, or other joints with a prosthetic assembly.

Figure 1:
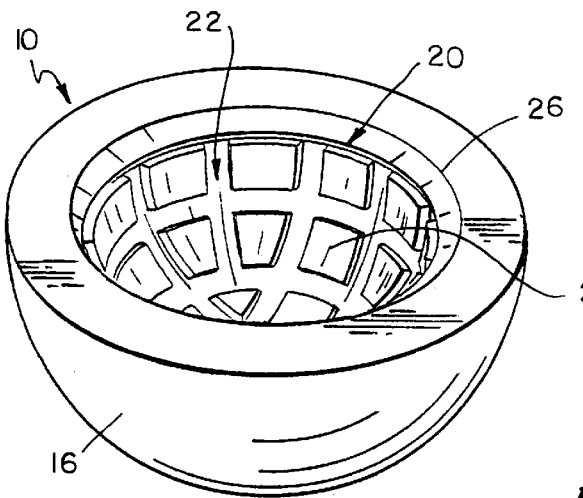
FIG. 1 is a perspective view of one embodiment of a bearing component in accordance with the present invention and showing an exterior and an opposite internal cavity defined by an interrupted articular face suitable for engaging a ball.

Referring to FIG. 1, an illustrative bearing component 10 is shown having an exterior suitable for engagement with the acetabulum or use with a support cup (not shown). Acetabular cups are mounted in the acetabulum using a variety of techniques, all well known in the orthopaedic field. While the illustrative bearing component 10 has an outer surface 16 which is generally hemispherical in shape to be received in a typical acetabular cup, it is contemplated that it may take on a variety of forms in order to cooperate with either the acetabulum or with the acetabular support cup. For an example of technique for mounting the bearing 10 in a support cup, see U.S. Pat. No. 5,049,158 to Engelhardt et al., relevant portions of which are incorporated herein by reference. The bearing component 10 may be mounted within the support cup, or even in the acetabulum however, using a variety of known attachment methods. See for example U.S. Pat. No. 4,904,265 to MacCollum, et al. and U.S. Pat. No. 5,002,577 to Bolesky et al.

Referring again to FIG. 1, the bearing component 10 illustratively comprises an interior 20 which forms an internal cavity 22 suitable for receiving a femoral head (not shown) therein and a one-piece interrupted articular face 24 for engagement and articulation with the femoral head. The term "one-piece" is used herein to mean that the articular face is itself shaped, molded, or formed to include said interruptions. The interrupted articular face 24 of the bearing component 10 minimizes available surface area of articulation with the femoral head. Illustratively, the interior 20 of bearing component 10 includes a mouth 26 extending about the internal cavity 22 and the circumference of the face 24. See FIG. 1. This mouth 26 of bearing component 10 defines a plane through which the femoral head enters the interior 20 of the bearing component 10 for engagement and articulation with the interrupted articular face 24.

The embodiments of one bearing component in accordance with the present invention that are illustrated in FIGS. 1–8 are formed for use with an acetabular prosthetic joint. However, as will be subsequently discussed, it is contemplated that specific patterns of interruptions within the articular face 24 may also be incorporated into a glenoid, patellar, femoral, humoral, tibial, ulnar, radial, wrist, and/or ankle component for a prosthetic joint assembly.

It is understood that the bearing component in accordance with the present invention can be made from any material that is biocompatible and which will undergo articulating movement with a corresponding natural or prosthetic member. For example, the bearing component could be formed from a variety of metals, plastics, ceramics, or composite materials. In the event that plastics are chosen, a high density polyethylene may be used, although numerous types of plastics may be suitable for purposes of the invention so long as the material provides both strength and a low-friction articulation surface for the corresponding joint face. Further, the bearing component in accordance with the present invention is constructed in accordance with well known methods of manufacture. For example, it is understood that a metal shell can be cast, forged, or machined to include the interrupted articular face while ceramic, plastic, and composite materials suggest other well-known methods of manufacture.

In one embodiment of the bearing component, the interrupted articular face 24 of the interior 20 includes a smooth spherically concave, generally hemispherical bearing surface 30 and a plurality of recess 32 formed within the surface 30. See FIGS. 1–4 and 6–8. It is understood that recesses may be formed and positioned in a variety of manners so long as the surface area of articulation is reduced from that of an uninterrupted smooth articular face (not shown) for an equivalently sized bearing component.

Figure 2:
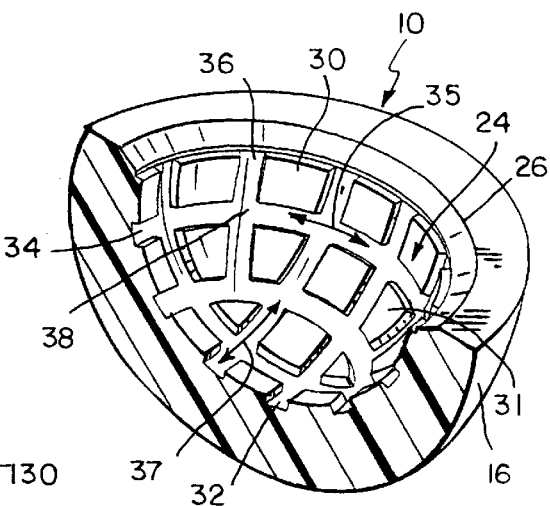
FIG. 2 is a cross-sectional view of the bearing component of FIG. 1 showing an interior of the bearing component including a mouth which defines the internal cavity and the interrupted articular face of the internal cavity having a generally hemispherical bearing surface and a plurality of intersecting grooves extending into the surface.

As best shown in FIG. 2, the recesses 32 may be formed as grooves 34, 36. Illustratively, the bearing surface 30 is defined by a plurality of bearing platforms 31 integral with the face 24 and grooves 34 extending about bearing surface 30 and between the platforms 31 substantially parallel as shown by arrow 35, to the mouth 26. Additionally, the interrupted articular face 24 includes grooves 36 extending between the platforms 31 substantially perpendicular, as shown by arrow 37, relative to the mouth 26. Thus, grooves 34, 36 illustratively cross one another at intersections 38. Grooves 34, 36 are positioned in spaced-apart relation to one another about the bearing surface 30 of the interrupted articular face 24. However, it is contemplated that grooves 34, 36 may vary in number and positioning about the surface 30 of the interrupted articular face 24.

Figure 3:
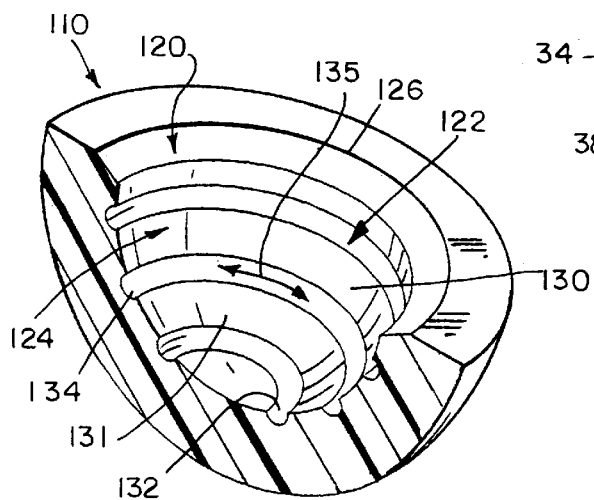
FIG. 3 is a cross-sectional view similar to FIG. 2 of another embodiment of a bearing component according to the present invention showing the interrupted articular face having a generally hemispherical bearing surface and a plurality of grooves extending into the surface substantially parallel to the mouth.

Another embodiment of the bearing component is illustrated in FIG. 3. The bearing component 110 includes an interior 120 forming an internal cavity 122 and a mouth 126 extending about the cavity 122. Further, the interior 120 includes a one-piece interrupted articular face 124. The interrupted articular face 124 has a bearing surface 130 defined by a plurality of bearing platforms 131 integral with the face 124 and a plurality of recesses 132 that extend into the surface 130. The recesses 132 are formed as grooves 134 extending about the bearing surface 130 between the platforms 131 substantially parallel, as shown by arrow 135, to the mouth 126. Illustratively, the grooves 134 are positioned in spaced-apart relation to one another about the bearing surface 130 of the face 124.

Figure 4:
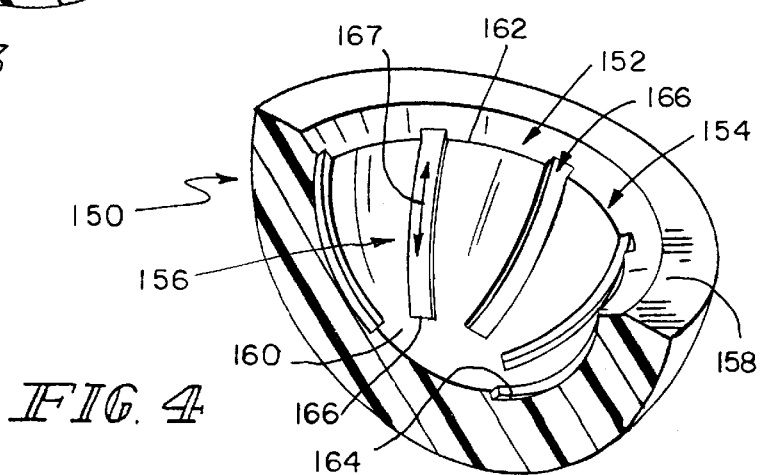
FIG. 4 is a cross-sectional view similar to FIG. 2 of another embodiment of a bearing component according to the present invention showing the interrupted articular face having a generally hemispherical bearing surface and a plurality of grooves extending into the surface substantially perpendicular to the mouth.

Yet another embodiment of the present invention is illustrated in FIG. 4. A bearing component 150 includes an interior 152 which forms an internal cavity 154 and a one-piece interrupted articular face 156. Additionally, the interior 152 includes a mouth 158 extending about the cavity 154. The interrupted articular face 156 of the interior 152 includes a generally hemispherical bearing surface 160 defined by a plurality of bearing platforms 162 integral with the face 156 and recesses 164 formed as grooves 166 extending about the surface 160 between platforms 162 and substantially perpendicular, as shown by arrow 167 to the mouth 158. Moreover, the grooves 166 are illustratively positioned in spaced-apart relation to one another about the bearing surface 160 of the face 156.

Figure 5:
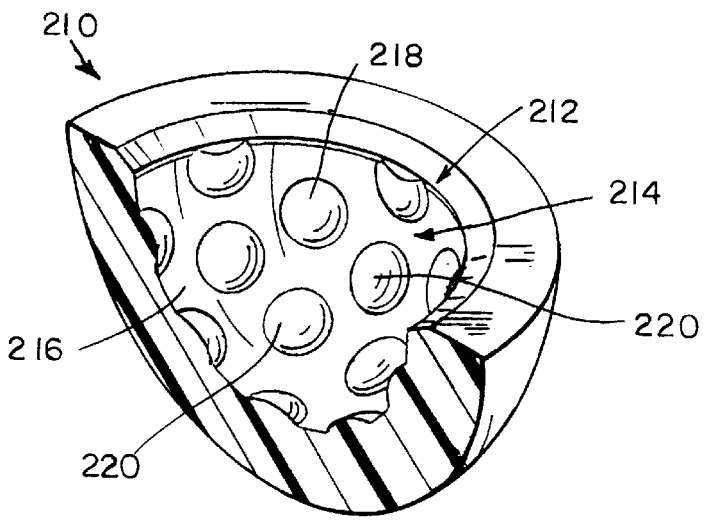
FIG. 5 is a cross-sectional view similar to FIG. 2 of another embodiment of a bearing component according to the present invention showing the interrupted articular face having a generally hemispherical bearing surface defined by a plurality of bearing platforms integral with the face and protruding into the internal cavity.

In another embodiment of the present invention, shown in FIG. 5, a bearing component 210 includes an interior 212 that forms an internal cavity 214 and a one-piece interrupted articular face 216. Illustratively, the articular face 216 is formed to include a generally hemispherical bearing surface 218 defined by a plurality of bearing platforms 220 integral with the face 216 and protruding into the cavity 214. Thus, the femoral head (not shown) will engage and articulate upon platforms 220 of the interrupted articular face 216 upon insertion into the cavity 214 of the bearing component 210. Illustratively, the platforms 220 are positioned in spaced-apart relation to one another about the interrupted articular face 216. It is understood that while the platforms 220, as shown in FIG. 5, are generally convex in shape, they may take on a number of forms so long as a low friction articular face 216 is provided for the femoral head.

Figure 6:
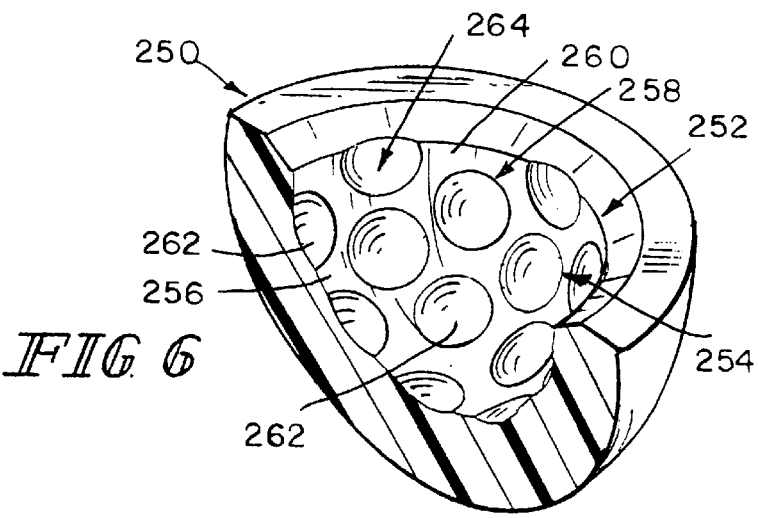
FIG. 6 is a cross-sectional view similar to FIG. 2 of another embodiment of a bearing component according to the present invention showing the interrupted articular face having a generally hemispherical bearing surface and a plurality of concave dimples extending into the bearing surface.

Further, another embodiment of the present invention is illustrated in FIG. 6. A bearing component 250 includes an interior 252 having an internal cavity 254 and a one-piece interrupted articular face 256. The interrupted articular face 256 includes a smooth generally hemispherical bearing surface 260 defined by a plurality of bearing platforms 258 integral with the face 256. Moreover, generally concave dimples 262 extend into the face 256 between the platforms 258 to interrupt the surface 260. The dimples 262 define a plurality of recesses 264 formed into the surface 260 of the interrupted articular face 256. Moreover the dimples 262 are illustratively positioned in spaced-apart relation to one another about the bearing surface 260 of the interrupted articular face 256.

Figure 7:
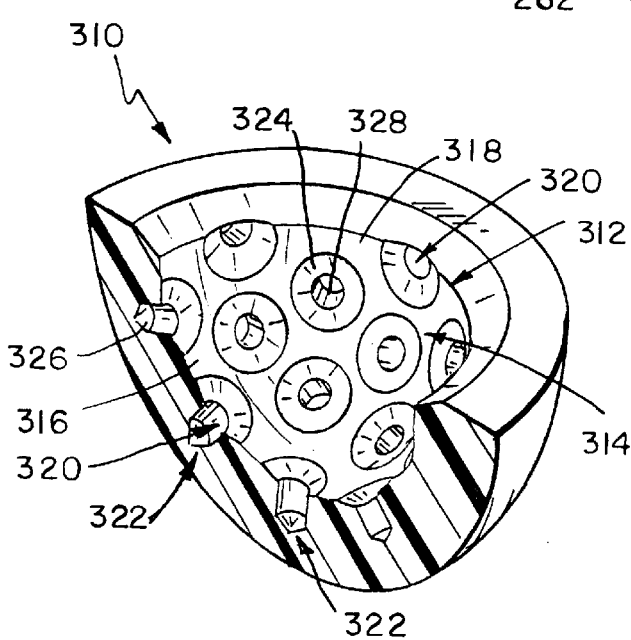
FIG. 7 is a cross-sectional view similar to FIG. 2 of another embodiment of a bearing component according to the present invention showing the interrupted articular face having a generally hemispherical bearing surface and a plurality of sockets extending into the bearing surface.

Another embodiment of the present invention is illustrated in FIG. 7. The bearing component 310 includes an interior 312 having an internal cavity 314 and a one-piece interrupted articular face 316. The articular face 316 includes a smooth generally hemispherical bearing surface 318 and a plurality of sockets 320 defining recesses 322 extending into the surface 318. Each socket 320 includes a conical-shaped mouth 324, a conical-shaped base 326, and a cylindrical side wall 328 extending between the mouth 324 and the base 326. Illustratively, the sockets 322 are positioned in spaced-apart relation to one another about the bearing surface 318 of the articular face 316. However, it is contemplated that the number and positioning of the sockets 322 may be varied.

Figure 8:
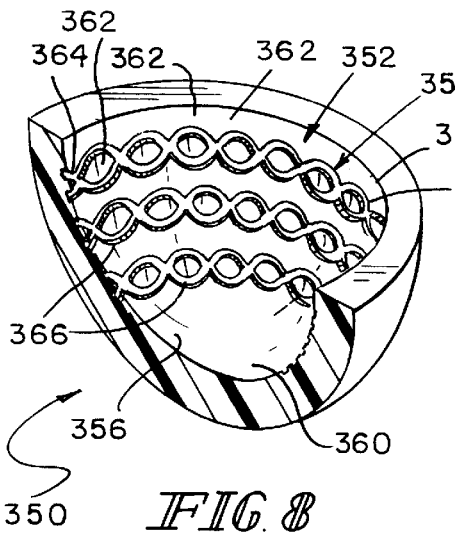
FIG. 8 is a cross-sectional view similar to FIG. 2 of another embodiment of a bearing component according to the present invention showing the interrupted articular face having a generally hemispherical bearing surface and a plurality of grooves extending into the surface and randomly weaving thereabout.

Another bearing component in accordance with the present invention is illustrated in FIG. 8. The bearing component 350 illustratively comprises an interior 352 which forms an internal cavity 354 suitable for receiving a femoral head (not shown) therein and a one-piece interrupted articular face 356 for engagement and articulation with the femoral head. The interrupted articular face 356 of the bearing component 350 minimizes available surface area of articulation with the femoral head.

Illustratively, the interior 352 of bearing component 350 includes a mouth 358 extending about the circumference internal cavity 354. See FIG. 8. This mouth 358 of bearing component 350 defines a plane through which the femoral head enters the interior 352 of the bearing component 350 for engagement and articulation with the interrupted articular face 356. The interrupted articular face 356 of the interior 352 includes a smooth generally hemispherical bearing surface 360 defined by a plurality of bearing platforms 362 and a plurality of recesses 364 formed therein between the platforms 362. Referring to FIG. 8, the bearing surface 360 is integral with the face 356 and grooves 366 weave about bearing surface 360 and between the platforms 362.

Figure 9:
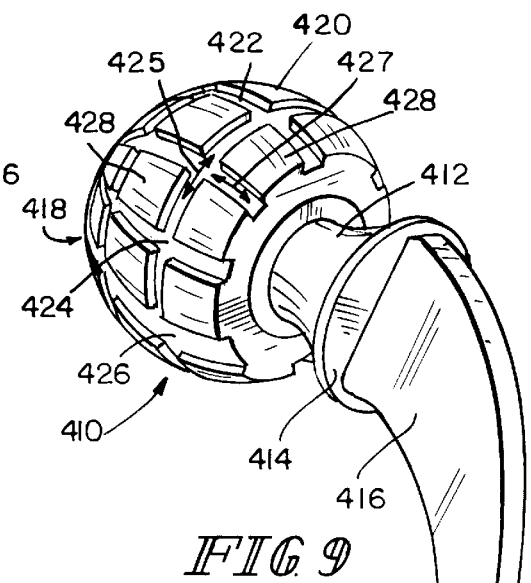
FIG. 9 is a perspective view of another embodiment of a bearing component in accordance with the present invention showing a ball attached to a stem and the ball including an interrupted articular face having a bearing surface and a plurality of intersecting groove extending into the surface.

Another bearing component in accordance with the present invention is illustrated in FIG. 9. A ball head bearing component 410 is provided for attachment to a neck 412. The neck 412 is connected to a platform 414 which is then connected to an arcuate stem or shaft 416. The ball head component 410 is insertable into the acetabular socket of the pelvis (not shown) once the prosthesis has been securely anchored in the femur. The ball head component 410 is designed to work equally well with a natural acetabular socket or with any variety of artificial acetabular cups. As with all other embodiments of the present invention, the dimensions of the ball head 410 can be easily varied to adapt to the particular bone structure of the patient or to the dimensions of the corresponding implanted prosthetic component. While a ball head component 410 is illustratively used as a hip joint prosthesis, it is contemplated that the ball head component, in accordance with the present invention could also be formed as a humeral head (not shown) for a shoulder joint prosthesis. For further description of a ball head see U.S. Pat. No. 4,068,216 Townley et al., relevant portions of which are incorporated herein by reference.

The ball head component 410 comprises a one-piece interrupted articular socket-engaging face 418 which reduces surface area of articulation between the ball 410 and the corresponding socket (not shown). The interrupted articular socket-engaging face 418 of the ball head component 410 includes a smooth spherically convex, generally hemispherical bearing surface 420 and a plurality of recess 422 formed within the surface 420. Illustratively, the recesses 422 are formed as grooves 424, 426. The bearing surface 420 is defined by a plurality of bearing platforms 428 integral with the face 418 and the grooves 424, 426 extend between the platforms 428. Preferably grooves 424 extend in the direction shown by arrow 425 and grooves 426 extend as shown by arrow 427 between the platforms 428. It is understood that the grooves 424, 426 may extend about the bearing surface 420 in a variety of manners, so long as the surface area of articulation between the ball 410 and the corresponding socket is reduced.

Figure 10:
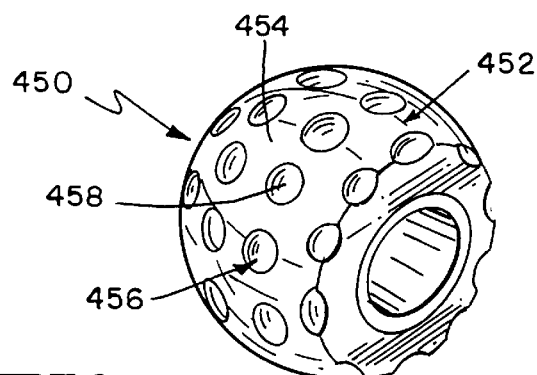
FIG. 10 is a perspective view of a bearing component in accordance with the present invention showing a ball including an interrupted articular face having a plurality of concave dimples extending into the surface.

Another embodiment of the bearing component in accordance with the present invention is illustrated in FIG. 10. A ball head component 450 includes a one-piece interrupted articular socket-engaging face 452 which reduces surface area of articulation between the ball 450 and the corresponding socket (not shown). The interrupted articular socket-engaging face 452 of the ball head component 450 includes a smooth generally spherical bearing surface 454 and a plurality of recess 456 formed within the surface 454. Illustratively, the recesses 456 are formed as generally concave dimples 458 and extend into the surface 454. Illustratively, the recesses 456 are formed similarly to the dimples 262 shown in FIG. 6.

Figure 11:
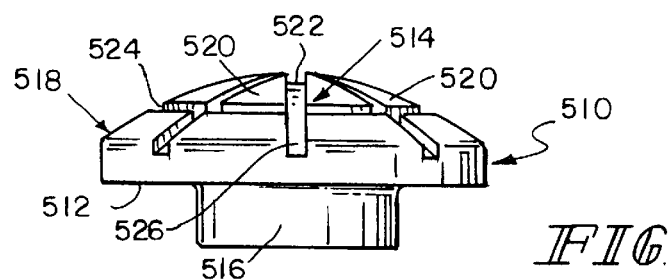
FIG. 11 shows an elevational view of another embodiment a bearing component in accordance with the present invention showing a patellar implant having an articular face interrupted by a plurality of bearing platforms with grooves extending therebetween.

Another embodiment of the bearing component in accordance with the present invention is illustrated in FIG. 11. A patellar joint bearing component 510 comprises a bone facing surface 512 and a one-piece interrupted articular surface 514 opposite the bone facing surface 512. Additionally, a protuberance 516 extends from the bone facing surface 512. For further description of a patellar joint implant see U.S. Pat. No. 4,964,867 to Boger, relevant portions of which are incorporated herein by reference. The interrupted articular surface 514 of the patellar joint implant 510 minimizes available surface area of articulation with the femoral component of the knee (not shown). The interrupted articular face 514 includes a smooth generally convex bearing surface 518 defined by a plurality of bearing platforms 520 integral with the face 514 and a plurality of recess 522 formed within the surface 518. Illustratively the recesses 522 are formed as grooves 524, 526 that extend between the platforms 520. It is understood that the surface 514 may be interrupted in a variety of manners, see for example FIGS. 2–8, so long as the surface area of articulation between the patellar implant 510 and the corresponding femoral component (not shown) is reduced.

Figure 12:
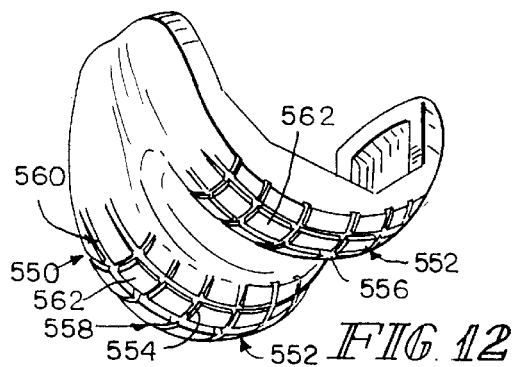
FIG. 12 is a perspective view of another embodiment of the present invention showing a prosthetic bearing component for an extreme distal end of the femur, and the bearing component having interrupted condyles.

An additional embodiment of the bearing component in accordance with the present invention is illustrated in FIG. 12. A prosthetic femoral bearing component 550 is provided which is adapted to replace the extreme distal portion of a femur (not shown). The femoral portion 550 is formed to cooperate with either a natural femur or a femoral prosthetic device such as that illustrated in U.S. Pat. No. 4,822,366, relevant portions of which are incorporated herein by reference. The bearing component 550 comprises on its surface two interrupted condyles or interrupted articular surfaces 552 that are configured to replace the condyles of the distal portion of the femur (not shown). The interrupted condyles 552 minimize available surface area of articulation with either a natural tibia or a prosthetic tibial bearing component. While the illustrative bearing component is shown as being suitable for use with the tibia, it is contemplated that it may take on a form in order to cooperate with the radius and/or ulna or a radial and/or ulnar prosthesis. It is also understood that the bearing components illustrated in FIGS. 12–15 may also be used in conjunction with the extreme distal portion of the humerus. The interrupted condyles 552 of the bearing component 550 include a smooth concave bearing surface 554 and a plurality of recesses 556 formed within the surface 554. Referring to FIG. 12, the recesses 556 are formed as grooves 558, 560. The bearing surface 554 is defined by a plurality of bearing platforms 562 integral with the face 552 and the grooves 558, 560 extend between the platforms 562. It is understood, that the grooves 558, 560 may extend about the bearing surface 554 in a variety of manners, so long as the surface area of articulation between the bearing component 550 and the corresponding tibial bearing component (not shown) is reduced.

Figure 13:
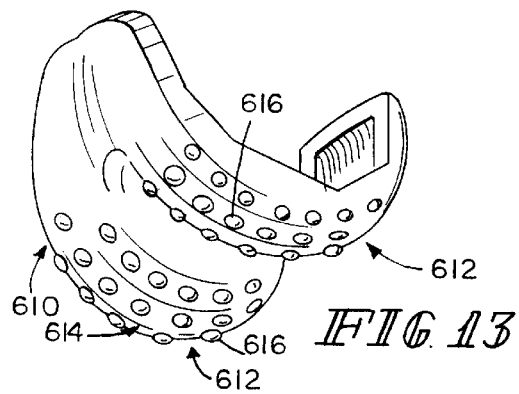
FIG. 13 is a perspective new similar to FIG. 12 of another embodiment of the present invention showing the interrupted condyles having a plurality of bearing platforms integral with the face and protruding therefrom.

Referring now to FIG. 13, an additional embodiment of the present invention includes a prosthetic femoral bearing component 610. The bearing component 610 comprises on its surface two interrupted articular surfaces 612. The interrupted articular surfaces 612 include a smooth surface 614 and a plurality of bearing platforms 616 integral with the surface 614. Illustratively, the platforms 616 are positioned in spaced-apart relation to one another about the interrupted articular surface 612. It is understood that while the platforms 616, as shown in FIG. 13, are generally convex in shape, similar to the platforms 220 illustrated in FIG. 5, they may take on a number of forms so long as a low friction articular face is provided for the corresponding component.

Figure 14:
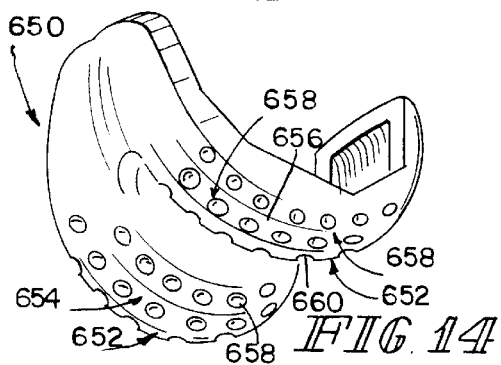
FIG. 14 is a perspective view similar to FIG. 12 of another embodiment of the present invention showing the interrupted condyles having a plurality of concave dimples extending therein.

An additional embodiment of the present invention is illustrated in FIG. 14. A femoral bearing component 650 is provided which comprises two interrupted articular surfaces 652. Each articular surface 652 includes a smooth bearing surface 656 that is defined by an interrupted bearing platform 654 for the accompanying articulating member. Moreover, generally concave dimples 658 extend into the surface 652 to interrupt the platform 654. The dimples 658 define a plurality of recesses 660 formed into the surface 656 of the interrupted articular surface 652. Moreover the dimples 658 are illustratively positioned in spaced-apart relation to one another about the bearing surface 652.

Figure 15:
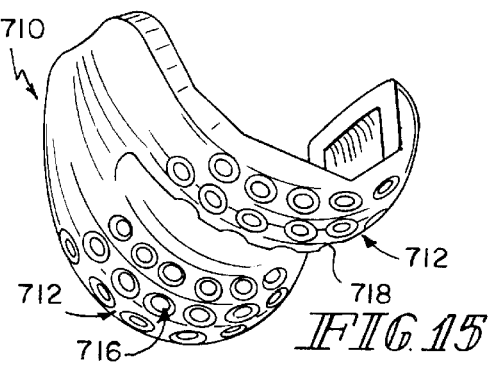
FIG. 15 is a perspective view similar to FIG. 12 of another embodiment of the present invention showing the interrupted condyles having a plurality of sockets extending therein.

Further, as illustrated in FIG. 15, an additional embodiment of the present invention is provided. A bearing component 710 is provided which comprises two interrupted articular surfaces 712. Each articular surface 712 is formed to include a plurality of sockets 716 defining recesses 718 that extend into the surface 714. Each socket 716 is illustratively formed as the sockets 312 of FIG. 7.

Figure 16:
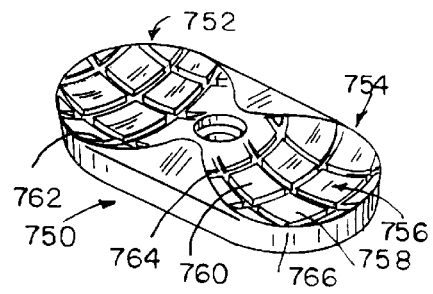
FIG. 16 is a perspective view of yet another embodiment of the present invention showing a prosthetic bearing component for an extreme proximal end of the tibia and the bearing component showing two slightly concave interrupted bearing surfaces corresponding to the medial and labial condyles of the tibia.

An additional embodiment of the present invention is illustrated in FIG. 16. A tibial bearing component 750 is provided to replace the extreme proximal portion of the tibia (not shown). The tibial bearing component insert 750 comprises two interrupted slightly concave bearing surfaces 752, 754 that are designed to replace the medial and lateral condyles of the tibia (not shown). The interrupted bearing surfaces 752, 754 are adapted to support and mate with the articular surfaces on the femoral component (not shown). For a further description of the articulating movement of a prosthetic tibial bearing component insert 750 suitable for use with the present invention, see U.S. Pat. No. 4,822,366, to Bolesky relevant portions of which are incorporated herein by reference. It is further contemplated that components such as those illustrated in FIGS. 16–19 could be adapted for use with the extreme proximal portion of the radius and/or ulna.

An interrupted articular face 756 includes a smooth concave bearing surface 758 defined by a plurality of bearing platforms 760 integral with the face 756 and a plurality of recess 762 formed within the surface 758 between the platforms 760. Illustratively, the recesses 762 are formed as grooves 764, 766. The grooves 764, 766 illustratively extend between the platforms 760. It is understood, that the grooves 764, 766 may extend about the bearing surface 758 in a variety of manners, so long as the surface area of articulation between the femoral component 750 and the corresponding tibial bearing component (not shown) is reduced.

Figure 17:
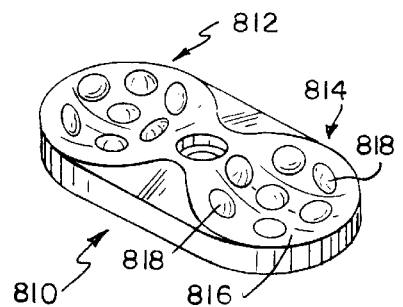
FIG. 17 is a perspective view similar to FIG. 16 of another embodiment of the present invention showing the interrupted bearing surfaces having a plurality of bearing platforms integral with the surfaces and protruding therefrom.

An alternative embodiment of a tibial bearing component insert 810 of the present invention is illustrated in FIG. 17. The tibial bearing component insert 810 includes two one-piece interrupted slightly concave articular surfaces 812, 814. The interrupted articular surfaces 812, 814 include a concave bearing surface 816 and a plurality of bearing platforms 818 integral with the surface 816. Illustratively, the bearing platforms 218, 616 are formed similarly to those shown in FIGS. 5 and 13 respectively.

Figure 18:
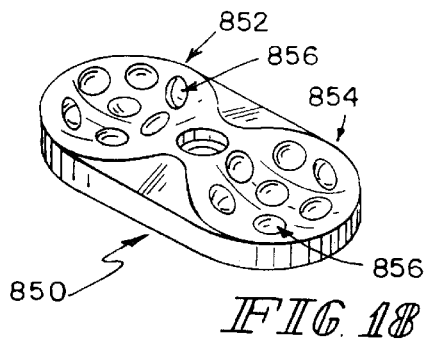
FIG. 18 is a perspective view similar to FIG. 16 of another embodiment of the present invention showing the interrupted bearing surfaces having a plurality of concave dimples extending therein.

Yet another embodiment of a tibial bearing component insert 850 of the present invention is illustrated in FIG. 18. The tibial bearing component 850 includes two one-piece interrupted slightly concave articular surfaces 852, 854. Each articular surface 852, 854 is formed to include generally concave dimples 856 extending into the surface 852, 854 so that corresponding members engage and undergo articulating movement on the surfaces 852, 854. The dimples 856 are formed similarly to the dimples 262, 456, and 658 shown in FIGS. 6, 10, and 14 respectively.

Figure 19:
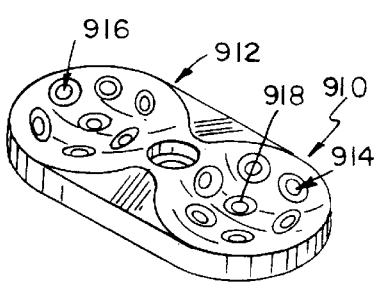
FIG. 19 is a perspective view similar to FIG. 16 of another embodiment of the present invention showing the interrupted bearing surfaces having a plurality of sockets extending therein.

A further embodiment of a tibial bearing component 910 of the present invention is shown in FIG. 19. the tibial bearing component 910 includes a one-piece interrupted articular surfaces 912, 914. Each articular surface 912, 914 is formed to include a plurality of sockets 916 defining recesses 918 that extend into the surface 912, 914. Each socket 916 is formed as sockets 320, 716 shown in FIGS. 7 and 15 respectively.

Bearing components in accordance with the present invention formed as acetabular sockets as shown in FIGS. 18 enable the physician to use large ball diameters for joint stability while minimizing surface area of articulation. For example, a bearing component is manufactured for use as an acetabular socket to produce an internal diameter (hereinafter "I.D.") of 32 mm with the surface area of a 28 mm I.D. or 22 mm I.D. by interrupting the articular face with recesses. Such a bearing component would have the joint stability of the 32 mm articulation and possibly the wear characteristics of the smaller I.D. It is believed that this decrease in surface area of articulation for the femoral head contributes the reduced production of joint debris. Thus, it decreases the production of joint debris in conventional prosthetic assemblies by replacing the conventional bearing component with an improved bearing component in accordance with the present invention having an interrupted articular face.

Further, bearing components in accordance with the present invention allow physicians to provide patients with prosthetic components with have reduced wear and greater stability within the body.

Although the invention has been described in detail with reference to certain preferred embodiments, variations and modifications exist within the scope and spirit of the invention as described and defined in the following claims.

What is claimed is:

1. A bearing component for a prosthesis, said bearing component comprising an interrupted articular face constructed of a plastics material suitable for mating with a corresponding joint face, the interrupted articular face includes a mouth extending about a circumference of the face, at least one recess intersecting the mouth and a bearing surface being defined by at least one bearing platform integral with the articular face and suitable to engage the corresponding joint face and to permit movement therewith.

2. The bearing component of claim 1, wherein the recess is formed as a groove extending about the bearing surface and through the bearing platform.

3. The bearing component of claim 1, wherein the interrupted articular face includes a plurality of recesses formed as grooves.

4. The bearing component of claim 3, wherein the grooves are positioned in spaced-apart relation to one another about the bearing surface.

5. The bearing component of claim 3, wherein the bearing surface is further defined by generally annular grooves that are positioned in an intersecting relationship relative to grooves about the bearing surface.

6. The bearing component of claim 1, wherein the recess is formed as a generally concave dimple in the bearing surface.

7. The bearing component of claim 6, wherein the interrupted articular face is formed to include a plurality of recesses formed as dimples, and the dimples are positioned in spaced-apart relation to one another about the bearing surface.

8. The bearing component of claim 1, wherein the recess is formed as a socket in the bearing surface and the socket includes a conical-shaped mouth, a conical-shaped base, and a cylindrical side wall extending between the mouth and the base.

9. The bearing component of claim 1, wherein said bearing surface being defined by a plurality of bearing platforms positioned in spaced-apart relation to one another about said interrupted articular face.

10. A bearing component for a prosthesis of the ball-joint type, said bearing component comprising an interior providing an internal cavity suitable for receiving a ball, said cavity being defined by a spherically concave interrupted articular face integral with the bearing component and suitable for engaging the ball, said bearing component further a mouth extending comprising about the internal cavity and the circumference of said interrupted articular face, said interrupted articular face being constructed of a plastics material and including at least one recess intersecting the mouth.

11. The bearing component of claim 10, wherein the interrupted articular face is formed to include a smooth generally hemispherical bearing surface wherein said at least one recess extending into the bearing surface.

12. The bearing component of claim 11, wherein the interior includes an annular lip extending about the circumference of the mouth and at least one groove extending about said bearing surface generally parallel to the lip.

13. The bearing component of claim 12, wherein the interrupted articular face is formed to include a plurality of grooves positioned in spaced-apart relation to one another about the bearing surface of the interrupted articular face.

14. The bearing component of claim 11, wherein said least one recess is formed as a groove extending generally perpendicular to an annular lip extending about the circumference of the mouth.

15. The bearing component of claim 14, wherein the interior includes at least one groove extending about the surface generally parallel to the lip and intersects at least one groove extending about said bearing surface generally perpendicular to the lip.

16. The bearing component of claim 14, wherein a plurality of grooves are formed to extend generally perpendicular to the lip in spaced-apart relation to one another about the bearing surface of the interrupted articular face.

17. The bearing component of claim 11, wherein the interior includes an annular lip extending about the circumference of the mouth and said at least one recess is formed as a groove positioned generally perpendicular to said lip.

18. The bearing component of claim 17, wherein a plurality of grooves are positioned in spaced-apart relation to one another about the bearing surface of the interrupted articular face.

19. The bearing component of claim 11, wherein the interrupted articular face includes generally concave dimples in the smooth bearing surface of the articular face and the dimples are formed to define the recesses within the bearing surface.

20. The bearing component of claim 19, wherein the dimples are positioned in spaced-apart relation to one another about the bearing surface of the articular face.

21. The bearing component of claim 11, wherein the interrupted articular face includes at least one socket extending into the bearing surface, each socket includes a conical-shaped mouth, a conical-shaped base, and a cylindrical side wall extending between the mouth and the base and the sockets are formed to define the recesses within the bearing surface.

22. A bearing component for a prosthesis of the ball-joint type, said bearing component comprising an interior providing an internal cavity suitable for receiving a ball, said cavity being defined by a spherically concave interrupted articular bearing face integral with the bearing component and suitable for engaging the ball, and a mouth extending about the internal cavity and the circumference of the face, said interrupted articular bearing face being constructed of a plastics material, and including a smooth generally hemispherical surface intersecting the mouth and including bearing platforms protruding into the internal cavity.

23. The bearing component of claim 22, wherein the bearing platforms are positioned in spaced-apart relation to one another about the smooth surface of the interrupted articular bearing face.

24. A prosthetic component assembly adapted for use in an acetabular cup fixed to the acetabulum, the assembly comprising a femoral element including a ball, and an acetabular bearing including an outer surface configured to be received in the acetabular cup and an interrupted articular face constructed of a plastics material adapted to mate with the ball of the femoral element, the interrupted articular face including a mouth extending about a circumference of said articular face and a bearing surface being defined by at least one bearing platform integral with the articular face and adapted to engage the corresponding ball to maximize available ball distribution and permit articulating movement of the ball within the bearing and at least one recess intersecting the mouth.

25. The prosthetic component of claim 24, wherein the recess is formed as a groove extending about the bearing surface and through the bearing platform.

26. The prosthetic component of claim 24, wherein the articular face includes a plurality of bearing platforms positioned to lie in spaced-apart relation to one another about the bearing surface.

* * * * *